United States Patent [19]

Lacy et al.

[11] 4,248,083
[45] Feb. 3, 1981

[54] CONTAINERLESS HIGH TEMPERATURE CALORIMETER APPARATUS

[75] Inventors: Lewis L. Lacy; Michael B. Robinson; Daniel B. Nisen, all of Huntsville, Ala.

[73] Assignee: The United States of America as represented by the Administrator of the National Aeronautics and Space Administration, Washington, D.C.

[21] Appl. No.: 53,569

[22] Filed: Jun. 29, 1979

[51] Int. Cl.³ .................................. G01K 17/00
[52] U.S. Cl. ................................... 73/190 R
[58] Field of Search ........................ 73/15 B, 190 R; 219/121 EB, 121 EF, 121 EG, 121 EM, 121 EP, 121 ER, 121 ES, 121 ET, 121 E

[56] References Cited

U.S. PATENT DOCUMENTS

| 2,880,483 | 4/1959 | Hanks et al. | 219/121 |
| 3,249,797 | 5/1966 | Donlevy | 219/121 |
| 3,403,007 | 9/1968 | Drangel et al. | 219/121 X |
| 3,527,081 | 9/1970 | Hill | 73/190 |
| 3,558,880 | 1/1971 | Kniseley | 219/121 X |

FOREIGN PATENT DOCUMENTS 2814951 6/1978 Fed. Rep. of Germany ............. 73/190

OTHER PUBLICATIONS

Hogan et al., Analytical Chemistry, vol. 32, #4, 4/60, pp. 573 & 574.

*Primary Examiner*—Herbert Goldstein
*Attorney, Agent, or Firm*—Joseph H. Beumer; John R. Manning; Leon D. Wofford, Jr.

[57] ABSTRACT

Containerless high temperature calorimeter apparatus is disclosed for measuring high temperature thermophysical properties of materials which includes a unique containerless heating apparatus wherein the specimen is suspended and heated by electron bombardment.

14 Claims, 3 Drawing Figures

CONTAINERLESS HIGH TEMPERATURE CALORIMETER APPARATUS

ORIGIN OF THE INVENTION

The invention described herein was made by employees of the United States Government and may be manufactured and used by or for the Government for Governmental purposes without the payment of any royalties thereon or therefor.

BACKGROUND OF THE INVENTION

Heretofore, calorimeter devices have been provided which have utilized either a hot crucible such as quartz, platinum, and refractory oxides or a cold crucible such as skull melting using actively cooled copper or tungsten crucibles. However, due to contact with the container wall, crucibles often introduce contamination into the samples which influence the measured properties. Therefore, techniques which use hot crucibles are limited to non-reactive metals and alloys. Furthermore, since crucibles are more likely to interact with reactive metals and alloys at higher temperatures, calorimeters using hot crucibles are generally limited to temperatures below twelve hundred degrees centigrade. To avoid contamination at temperatures above twelve hundred degrees centigrade, cold crucibles employing various skull melting techniques have been developed but none of the techniques offer sufficient control to serve as high temperature calorimeters.

Other disadvantages of cold crucibles are the usage of large amounts of power, introduction of severe thermal gradients in the sample resulting in severe convections and possible high loss of low vapor pressure elements.

To avoid the problem of contamination, the use of electromagnetic levitators has been proposed. However, these devices also require large amounts of power and do not provide sufficient temperature control or the capability to measure the precise power absorbed by the test specimen. These devices suffer severe convection currents caused by thermalgradients and non-linear coupling and consequently high vapor losses of low vapor pressure elements.

Accordingly, an important object of the present invention is to provide high temperature calorimeter apparatus which will measure thermophysical properties of a specimen at high temperatures with accurate test control.

Yet another important object of the present invention is to provide a high temperature calorimeter in which a wide range of thermophysical properties of materials can be determined.

Still another important object of the present invention is to provide a high temperature calorimeter which is containerless and will avoid the contamination of the specimen by interaction with container walls.

Still another important object of the present invention is the provision of a high temperature calorimeter apparatus for measuring the thermophysical properties of materials at high temperatures having a low power requirement.

Yet another important object of the present invention is the provision of heating apparatus for use in a containerless high temperature calorimeter in which convection currents are reduced and in which the specimen is isothermal.

SUMMARY OF THE INVENTION

It has been found according to the invention that high temperature containerless calorimeter apparatus can be provided by suspending the specimen in a vacuum container centrally between an electrode and grid arrangement wherein the specimen is heated by omnidirectional electron bombardment with accurate control.

The apparatus is capable of accurately measuring the emissivity of the solid and liquid phase at various high temperatures for a variety of metals and alloys. Since the device test alloys of different and known compositions, the device can be used to accurately determine the equilibrium phase-diagram of many different alloys and the melting points of many different metals and alloys. The specific heat of metals and alloys at various temperatures for both the liquid and solid phases can be determined. The heat of fusion of pure metals and alloys of various compositions can be accurately determined. The device can also be utilized to accurately determine surface tension and the density of molten metals and alloys.

BRIEF DESCRIPTION OF THE DRAWING

The construction designed to carry out the invention will be hereinafter described, together with other features.

The invention will be more readily understood from a reading of the following specification and by reference to the accompanying drawing forming a part thereof, wherein an example of the invention is shown and wherein.

DESCRIPTION OF A PREFERRED EMBODIMENT

Figure 1:
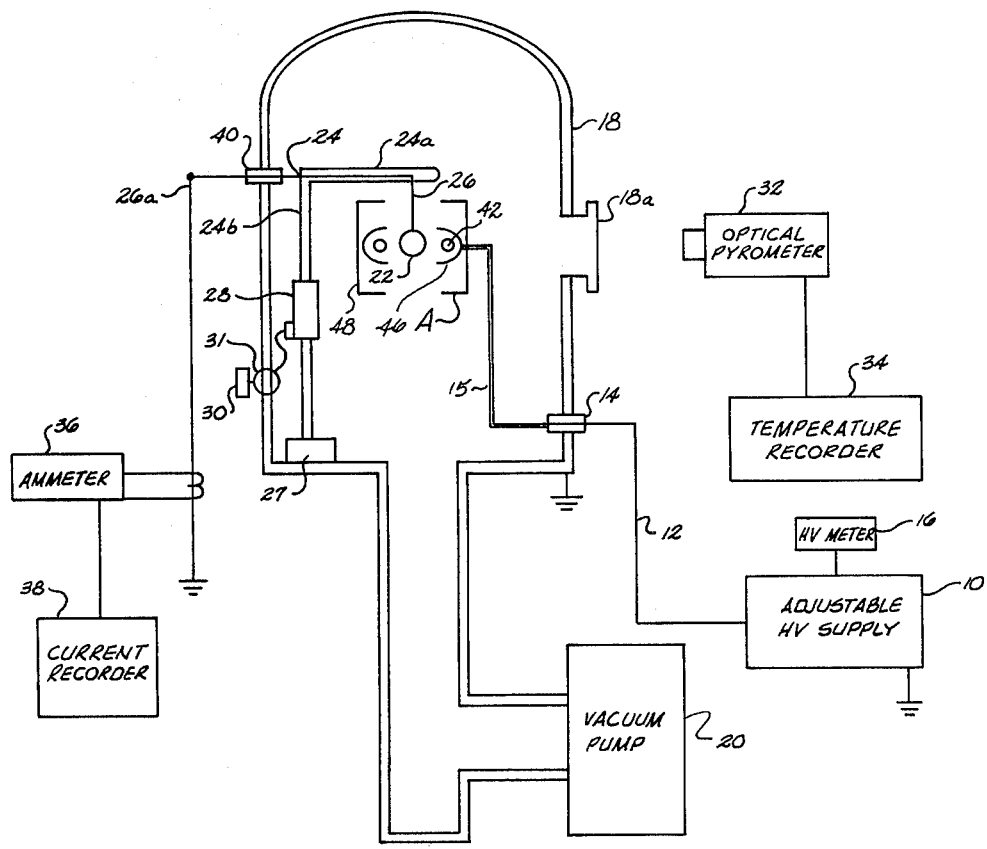
FIG. 1 is a schematic illustration of containerless high temperature calorimeter apparatus constructed according to the invention.
Figure 3:
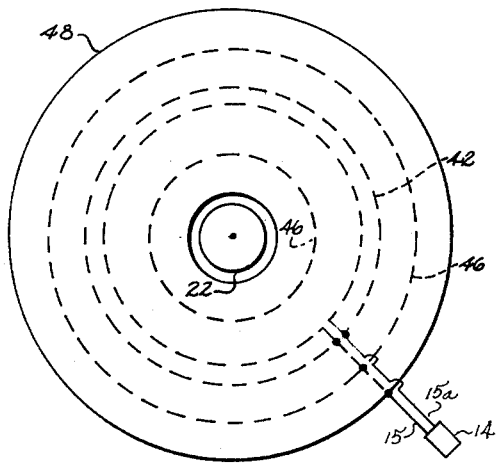
FIG. 3 is a schematic plan view of an electron bombardment heating apparatus according to the invention.

The drawing illustrates calorimeter apparatus for determining the thermophysical properties of materials which includes a vacuum container and heating cell apparatus A carried within the vacuum container. Support means are provided for positioning a specimen of the material within the heating cell apparatus including means for maintaining the specimen at ground potential. Electron emission means included in the heating cell apparatus and carried therein is adapted for connection to a power source whereby electrons are emitted by the electron emission means. Grid means included in the heating cell apparatus is carried about the electron emission means focusing and directing the emitted electrons in general alignment toward the specimen. The electron emission means and grid means are shaped so as to cause the emitted electrons to strike the specimen in an omnidirectional bombardment pattern providing uniform heating of the specimen and containment of the electrons.

A high voltage power supply is indicated at 10 such as a conventional electron beam power supply which may be normally operated at five thousand volts negative potential. The high voltage is supplied to the heating apparatus A by means of a pair of high voltage coaxial cables 12 through a high voltage vacuum feed through 14 and a pair of conductive copper tubes 15 which also serve to support the heating cell apparatus A. A high voltage meter 16 may be utilized so that the power setting may be set at a desired value. The heating apparatus A is supported in a vacuum bell jar 18 which is evacuated by a suitable vacuum pump 20. A sample specimen 22 is supported in suspended position inside the heating cell apparatus A by means of a cantilevered holder support 24 and is maintained at the ground potential by s support wire 26. The sample holder 24 stands on a base 27. The holder support 24 includes a cantilevered arm 24a by which support wire 26 is carried and a vertical standard 24b attached to base 27. The standard 24b is preferably provided in two-piece construction wherein the two sections are connected by means of a suitable gear box 28 having connection to a control box 30 by means of a rotating high vacuum feedthrough 31 by which the support 24a may be moved up and down to vary the position of the specimen relative to the heating apparatus and thus afford a degree of control over the heating and temperature of the specimen.

The vacuum bell jar 18 includes a window 18a having alignment with an optical pyrometer 32 which may be any conventional optical pyrometer. Temperature recorder 34 is connected to the pyrometer 32 for recording the temperatures of the specimen. Temperature recorder 34 may be any suitable analog or digital recording volt meter.

The power supplied to the sample specimen 22 can be accurately determined by reading high voltage meter 16 and the current flowing through the specimen by ammeter 36 which can also be supplied with a recorder in the form of a suitable current recorder which may be any suitable analog or digital recorder. The current supplied to the specimen flows through ground wire 26 which is terminated outside the bell jar by means of a high vacuum feedthrough 40 and electrical lead 26a which is connected through the current sensor 36 such that current flowing to ground may be recorded.

It is preferred that the cantilevered arm support portion 24a is made from an insulating material so that no current will flow through the arm. Other means, as will be hereinafter disclosed, are provided for limiting the movement and attraction of electrons solely to the specimen 22. In this manner, power is consumed solely in heating specimen 22 substantially reducing any waste of power resulting in achieving high specimen temperatures at low power requirements. Current recorded at 38 will be essentially solely due to electrons striking the sample specimen during bombardment and, hence, the heating of the specimen will be directly proportional to the measured current and power.

Figure 2:
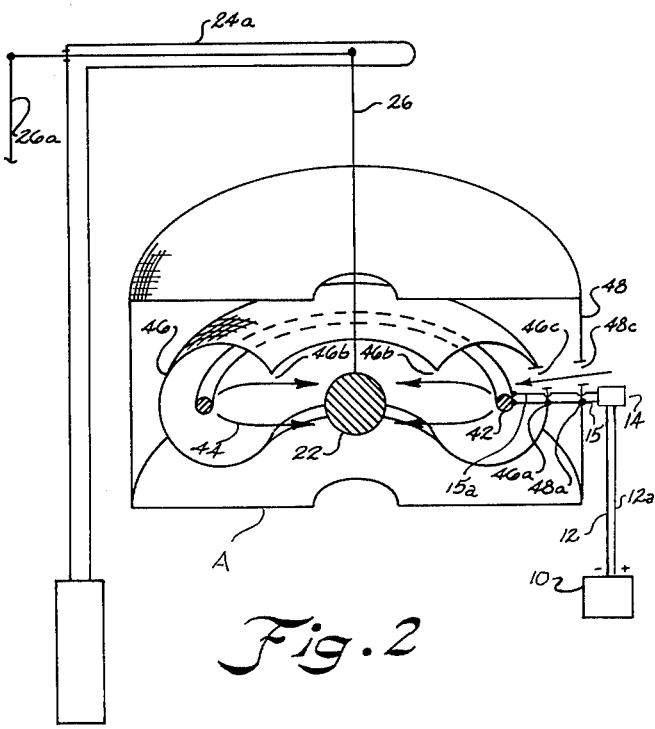
FIG. 2 is a schematic illustration illustrating an electron bombardment heating apparatus for a containerless high temperature calorimeter according to the invention.

Referring now to FIG. 2, the heating apparatus A is disclosed in more detail as including an annular cathode element 42 connected to high voltage power source 10 by means of coaxial cables 12, 12a and tubes 15, 15a which heats the cathode filament to incandensence. Thermionic electrons emitted by the cathode are transferred to the sample specimen 22 which is at ground potential. The bombarding electrons 44 striking the specimen are omnidirectional, as will be apparent hereinafter, and provide for a uniform heating of the sample with only a small thermal gradient. The electrons striking the specimen are focused or directed in general alignment therewith by a collimating grid means 46 which is held at the same negative potential as the cathode filament 42 by means of connection with incoming negative coaxial lead 12 and corresponding tube 15 at terminal 46a. The bombarding electrons are prevented from heating and melting the specimen supporting wire 26 by the utilization of the collimating grid 46 and an equipotential grid 48 which serves as grid container for the collimating grid and cathode. The equipotential grid 48 is maintained at the same negative potential as grid 46 and cathode 42 by means of connection with the incoming coaxial lead 12 and tube 15 at terminal 48a. The equipotential grid prevents the loss of electrons and subsequent heating of specimen support 24 and bell jar 18. Grids 46 and 48 are preferably constructed from a mesh material such as stainless steel and supported in their relative spacing by tube 15 within vacuum jar 18.

As illustrated, the cathode element 42 is advantageously formed as a ring-shaped element from any suitable material such as tungsten and is carried and positioned within the collimating grid 46 as illustrated being substantially enclosed therein. The collimating grid 46 is likewise toroidial shaped having an annular slot opening 46b formed in the inner annular periphery thereof through which the electrons are focused for bombarding the specimen. This form of the collimating grid has been found to provide exceptional results in focusing the electrons on the specimen during bombardment so as to avoid electron loss and subsequent striking of the support wire and other associated parts of the apparatus.

The temperature of the specimen can be accurately measured by the pyrometer and recorded. Slits 46c and 48c formed in the collimating and equipotential grids provide means for viewing the specimen through the window 18a by the pyrometer for temperature measurement. The heating power supplied to the specimen can be accurately determined by reading the high voltage meter 16 and the current flowing into the specimen by means of ammeter 36. Since the electrons which strike the sample are effectively prevented from flowing to ground except through ground wire 26 the measured current at detector 36 accurately reflects the power absorbed by the specimen as it is heated. The current conducted through the specimen is continuously recorded on recorder 38. From this information, the thermophysical properties of the specimen may be determined from known expressions and calculations.

The size and shape of the specimen is not critical and can be used in the form of wires, cylinders, disks, buttons, or spheres. The specimen support wire 22 consists of a high purity metal of one of the constituent elements. For Example, for making measurements on pure niobium and niobium alloys high purity niobium wire is used. The specimen sample can be attached to the support wire by several convenient means including spot welding or cutting a friction fit mortar slot into the sample. The temperature of the sample specimen can be accurately controlled by the use of the voltage and emission current controls on the power supply 10 and by the location of the specimen in the heating apparatus by the use of gear box 28.

As described previously, the high temperature calorimeter is capable of measuring the equilibrium thermodynamic parameters listed in the summary of the invention. To use the apparatus, the sample 22 is placed within the cell and heated to any desired temperature. Temperatures up to 3400 degrees centigrade have been obtained with the apparatus. In one example, a niobium-germanium alloy was tested consisting of 18 percent germanium wherein the specimen was heated through melting phase (approximately 2070 degrees C.) with a power consumption of approximately 18 watts.

To determine the emissivity of the sample, pyrometer 32 is used to determine that the sample is at a thermal equilibrium and is neither melting or freezing. At thermal equilibrium, this emissivity can be calculated by setting the power (watts) used to heat the specimen, which may be determined from the measurement of voltmeter 16 and ammeter 36, equal to a calculated value for the heat loss rate due to thermal radiation which may be calculated from a known expression for grey body radiation. The emissivity determined by this method must be used to determine the true temperature of the sample since the pyrometer measures only the "brightness" temperature. This technique can be used to measure the emissivity of both the solid and liquid phases. The emissivity of the material can be measured at different temperatures by changing the temperature of the sample to a higher or lower value.

Once the emissivity of the material is known, the specific heat of the solid material can be determined by slowly heating the sample and simultaneously measuring its rate of temperature change and the power or net heat absorbed by the sample. The melting temperature of the sample can be determined by visually monitoring the temperature where melting begins or determining if there is a sudden decrease in the rate of temperature change. If the composition of the alloy is previously known by chemical analysis, the high temperature equilibrium phase diagram can be determined by using the samples of various compositions.

The heat of fusion of the metal or alloy can be determined by accurately determining the power absorbed by specimen 22, the total time required for melting to take place, and the mass of the sample. The specific heat of the liquid phase can be determined at the completion of melting by determining the sudden increase in the rate of temperature change. This procedure works well if the melting temperatures of the alloy being investigated is less than the melting point of the wire support.

The surface tension of the molten metal or alloy can be measured by determining the critical mass of a pendulant drop which forms and is released by the support wire. An estimate of the density of the molten liquid can be made by photographing the pendulant drop using a camera of known magnification. This same photograph can also be used to determine the surface tension of the molten metal or alloy by the pendulant drop technique.

While a preferred embodiment of the invention has been described using specific terms, such description is for illustrative purposes only, and it is to be understood that changes and variations may be made without departing from the spirit or scope of the following claims.

What is claimed is:

1. Calorimeter heating apparatus for heating a specimen of a material in a calorimeter device for determining thermophysical properties of the material, comprising:
    a vacuum housing;
    an annular cathode element carried in said vacuum housing adapted for connection to a high voltage power source whereby electrons are emitted from said cathode element;
    support means for supporting specimens of different shapes and sizes closely adjacent said cathode element for bombardment by said emitted electrons;
    annular collimating grid carried adjacent said cathode element generally surrounding said cathode means so as to focus and direct the emission of electrons in general alignment toward said specimen for bombardment;
    equipotential grid means substantially enclosing said collimating grid means and cathode element containing said emitted electrons to prevent the loss of emitted electrons and any bombardment and heating of said support means and associated structure affording accurate heating of said specimen, said equipotential grid means including an opening through which said specimen may be inserted and positioned by said support means for heating; and
    said cathode element, collimating grid, and equipotential grid being operatively connected to common ground potential.

2. The apparatus of claim 1 wherein said collimating grid means has a toroidal shape and includes an annular slot opening around an inner periphery thereof, said annular slot opening around an inner periphery thereof, said annular cathode element being received in said toroidal grid element so as to emit electrons outwardly through said slot opening, and said specimen being supported in an open central portion of said toroidal grid means and annular cathode element whereby electrons strike said specimen in an omnidirection bombardment pattern providing uniform heating of said specimen.

3. The apparatus of claim 1 wherein said equipotential grid means includes a cylindrical grid element and said opening thereof is formed as a central aperture in an end surface thereof through which said specimen is supported.

4. The apparatus of claim 1 including viewing means formed in said housing and said collimating and equipotential grid means affording viewing of said specimen from outside said heating apparatus.

5. The apparatus of claim 1 wherein said support means includes a vertically adjustable support member by which said specimen is supported affording a desired vertical positioning of said specimen relative to said cathode means.

6. Calorimeter apparatus for determining thermophysical properties of a material comprising:
    a vacuum housing;
    a heating cell carried in said housing;
    support means for supporting specimens of said material of different shapes and sizes in said heating cell and including suspension means for suspending said specimen within said heating cell and maintaining said specimen at ground potential in a manner minimizing thermal gradients and maintaining said specimen substantially isothermal;
    electron bombardment means carried within said heating cell for heating said specimen;
    power source means connected to said electron bombardment means;
    temperature detecting means for measuring the temperature of said specimen; and
    current detecting means electrically connected with said suspension means and specimen for measuring the electrons striking said specimen.

7. The apparatus of claim 6 including grid means for focusing electrons emitted by said electron bombardment means in general alignment toward said specimen in an omnidirectional bombardment pattern and for limiting the movement of electrons so as to prevent the striking of said support means and the like.

8. Calorimeter apparatus for determining the thermophysical properties of materials comprising:
a vacuum container;
heating cell apparatus carried within said vacuum container;
support means for supporting specimens of said material in different shapes and sizes and positioning a specimen within said heating cell apparatus;
electron emission means included in said heating cell apparatus and carried within said cell apparatus adapted for connection to a power source whereby electrons are emitted by said electron emission means;
grid means included in said heating cell apparatus carried about said electron emission means focusing and directing said emitted electrons in general alignment toward said specimen;
said support means including suspension means for positioning said specimen entirely with said grid means and grounding said specimen resulting in reduced thermal gradients and maintainence of said specimen substantially isothermal; and
said electron emission means and grid means being shaped so as to cause said emitted electrons to strike said specimen in an omnidirectional bombardment pattern facilitating uniform heating of said specimen and containment of said electrons avoiding bombardment and loss of electrons through said support means.

9. The apparatus of claim 8 including temperature detecting means for measuring the temperature of said specimen.

10. The apparatus of claim 9 including current detector means for measuring the electron flow through said specimen to ground.

11. The apparatus of claim 8 wherein said support means includes an adjustable support member for adjusting the position of said specimen relative to said electron emission means affording control over the temperature of said specimen.

12. The apparatus of claim 8 wherein said electron emission means includes an annular cathode element circumscribing said specimen.

13. The apparatus of claim 12 wherein said grid means includes a toroidal-shaped grid element having an annular slot opening in the inner periphery thereof and said annular cathode element being received within said toroidal grid element so as to emit electrons through said slot opening toward said specimen.

14. The apparatus of claim 12 including a second grid means substantially enclosing said first mentioned grid means and said cathode means having an opening through which said specimen may be inserted and supported.

* * * * *